United States Patent [19]
Koshi

[11] 4,417,887
[45] Nov. 29, 1983

[54] CONNECTOR FOR CATHETER

[75] Inventor: Isei Koshi, Fujinomiya, Japan

[73] Assignee: Fuji Terumo Co., Ltd., Fujinomiya, Japan

[21] Appl. No.: 426,246

[22] Filed: Sep. 28, 1982

[30] Foreign Application Priority Data

Oct. 30, 1981 [JP] Japan .................................. 56-172929

[51] Int. Cl.$^3$ ................................................ A61M 5/00
[52] U.S. Cl. ..................................... 604/162; 604/192
[58] Field of Search ............... 604/192, 171, 162, 283, 604/263, 187, 158, 93

[56] References Cited

U.S. PATENT DOCUMENTS

| | | | |
|---|---|---|---|
| 3,536,073 | 10/1970 | Farb | 604/162 |
| 3,572,334 | 3/1971 | Petterson | 604/162 |
| 3,610,240 | 10/1971 | Harautuneian | 604/162 |
| 3,709,223 | 1/1973 | Macalalad et al. | 604/162 |

FOREIGN PATENT DOCUMENTS 54-132987 9/1979 Japan .

Primary Examiner—John D. Yasko
Attorney, Agent, or Firm—Frishauf, Holtz, Goodman and Woodward

[57] ABSTRACT

A connector for a catheter, which comprises a hub provided at the leading end thereof with a hollow needle tube; a cap capable of being detachably attached to the rear end of the hub and water-tightly sealing the interior of the hub; a sheath of the shape of a blind cylinder for admitting therein the aforementioned hub from the needle tube side and being slidably fitted around the outer side of the hub, the blind cylinder being provided in the closed end thereof with an aperture for permitting the needle tube to be thrust out therethrough; and a case of the shape of a blind cylinder for admitting therein the aforementioned sheath from the closed end side thereof and being detachably fitted around one end part of the sheath.

10 Claims, 7 Drawing Figures

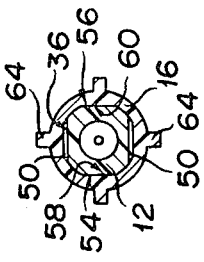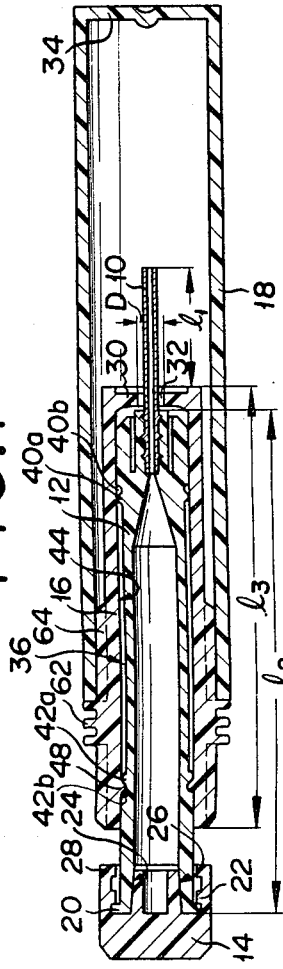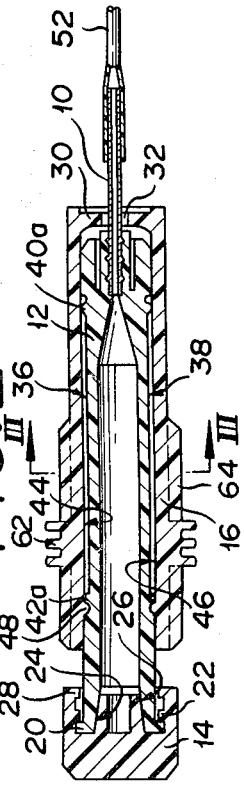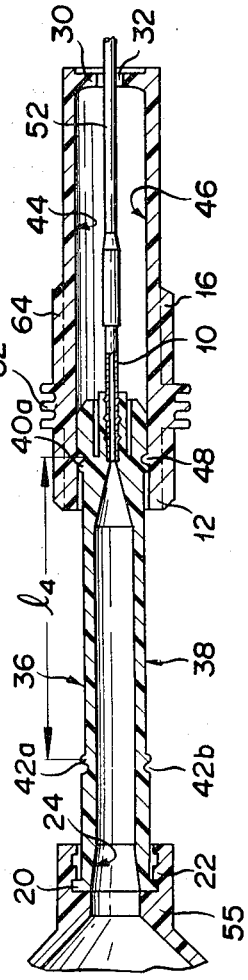

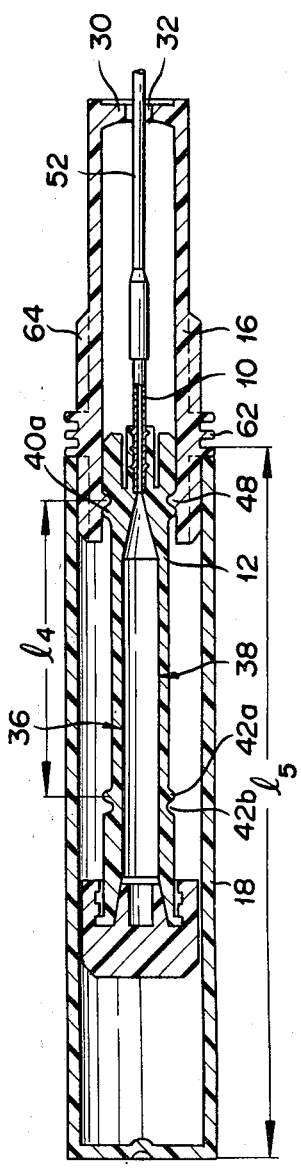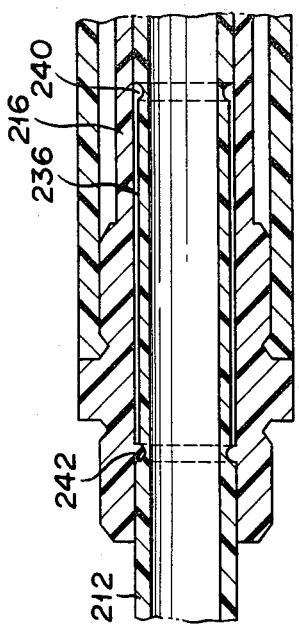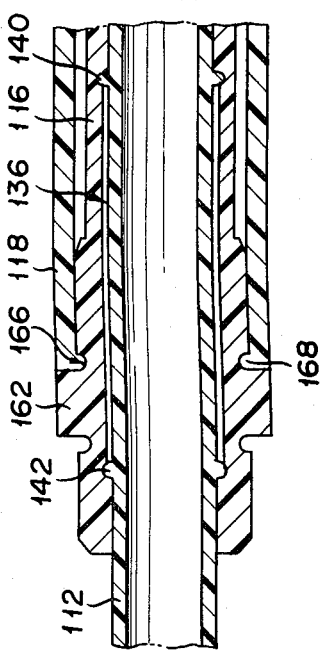

CONNECTOR FOR CATHETER

BACKGROUND OF THE INVENTION

1. Field of the Invention

This invention relates to a connector for a catheter. More particularly, this invention relates to a connector for a catheter, capable of providing required connection between a catheter and a needle adopted in a method for injecting a medicinal liquid such as anesthetic through the catheter inserted into the blood vessel or epidural cavity, particularly the hollow needle method, with perfect ease of operation without fear of possible contamination, accidental separation or breakage of the portions held in connection by the connector.

2. Description of Prior Art

For the insertion of a catheter into the blood vessel, the hollow needle method or the cut-down method is available. The former method involves securing the blood vessel with a puncturing needle which consists of a stainless steel inner needle and a catheter assembly adapted to serve as an outer needle for incasing the inner needle, extracting the inner needle, inserting the catheter via the interior of the outer needle into the blood vessel to be indwelled therein, subsequently extracting the outer needle and removing it clearly of the outer end of the catheter, and fitting to the outer end of the catheter a connector possessed of a connecting needle. The latter method comprises surgically exposing the blood vessel from the patient's body, incising a cut in the exposed blood vessel, and inserting a catheter through the cut into the blood vessel to be indwelled therein. The catheter used in this method is provided integrally at the outer end thereof with a connector possessed of a connecting needle. The hollow needle method, therefore, is utilized extensively in the high-calorie transfusion therapy and the continuous epidural anesthesia.

A variety of connectors have heretofore been suggested for use on the outer end of the indwelling catheter to be inserted such as into the blood vessel in accordance with the hollow needle method. Among these connectors is counted, for example, a connector which comprises a hollow needle tube, a hub fitted round the outer surface of one end of the needle tube, and a cap attached to the rear end of the hub. This particular connector, however, is destined to collect dust in the portion where the needle tube and the catheter are joined to each other. When the indwelling of the catheter in the blood vessel is prolonged, therefore, there may arise the possibility that the blood will be contaminated by leakage through the portion of connection or the possibility that the needle tube will be fractured, the catheter bent at the leading end of the needle tube, and the connector accidentally separated or fractured.

Another connector for the indwelling catheter comprises a needle tube, a hub fitted round one end of the needle tube, a cap attached to the rear end of the hub, a protective tube detachably fitted round the hub and adapted to protect the needle tube and the catheter, a lower case detachably fitted round the hub and wrapped round the outer side of the protective tube to provide double protection, and an upper case detachably fitted round the lower case and adapted to protect the cap airtightly. The connector of this construction indeed is free from the posibility of the blood being contaminated by leakage through the portion of connection between the needle tube and the catheter and the possibility of the needle tube being fractured or the catheter being fractured at the leading portion of the needle tube. It nevertheless has a disadvantage that assemblage of all these components entails a complicate work. Specifically, the operation of the catheter using this particular connector is highly troublesome because it entails a procedure which involves the steps of passing the catheter through the lower case and the protective tube, joining the catheter and the needle tube to each other, then fitting the protective tube and the lower case round the hub in the order mentioned, removing the cap, attaching a syringe to the hub, injecting a medicinal liquid, subsequently replacing the cap, and setting the upper case in position.

Yet another connector for the indwelling catheter comprises a needle tube, a hub fitted round one end of the needle tube, a cap attached to the rear end of the hub, and a protective cylinder adapted to be passed through the catheter before the connection between the needle tube and the catheter and, after the connection therebetween, to have the rear end thereof fitted round the outer side of the hub and the other end thereof fastened so as to support the catheter in position (Utility Model Koaki Publication SHO-54(1979)-132,987). Similarly to the second connector cited above, this connector is free from the possibility of the blood being contaminated by leakage through the portion of connection between the needle tube and the catheter and the possibility of the needle tube being fractured or the catheter being bent and fractured at the forward end of the needle tube. It nevertheless has a disadvantage that was assemblage of this connector entails a complicate procedure comprising the steps of preparatorily separating the hub from the protective cylinder, fitting it round the catheter, connecting the catheter to the needle tube, and thereafter fitting the protective tube round the hub. It is also liable to expose the blood to contamination by leakage through the cap's side.

It is, therefore, an object of this invention to provide a novel connector for a catheter.

Another object of this invention is to provide a connector for the catheter, which permits the needle tube and the catheter to be connected to each other simply and quickly, enables the cap to be doubly sealed tightly and, at the same time, precludes the possibility of contamination being caused by leakage through the portion of connection between the needle tube and the catheter and the possibility of the catheter being fractured at the portion of connection at the leading end of the needle tube.

SUMMARY OF THE INVENTION

The objects described above the accomplished by this invention providing a connector for a catheter, which comprises a hub provided at the leading end thereof with a hollow needle tube, a cap capable of detachably attaching itself to the rear end of the aforementioned hub and water-tightly sealing the interior of the hub, a sheath of the shape of a blind cylinder for admitting therein the aforementioned hub from the needle tube side while allowing itself to be slidably fitted round the outer side of the hub, the blind cylinder being provided in the closed end thereof with an aperture for permitting the needle to be to be thrust out therethrough, and a case of the shape of a blind cylinder for admitting therein the aforementioned sheath from the closed end side thereof while allowing itself to be detachably fitted round one end part of the sheath, the hub and the sheath having relative lengths such that the hub may be free to move inside the sheath from the position at which the needle tube is fully thrust out through the orifice to the position at which it is wholly embraced within the sheath, the hub and the sheath being provided on the outer and inner surfaces thereof respectively with stop means capable of stopping the hub and the sheath relative to each other at the position at which the needle tube is fully thrust out though the orifice to the position at which it is wholly embraced within the sheath, the orifice having a diameter such that when the needle tube thrust out through the orifice is retracted to be embraced again within the sheath, the catheter meanwhile fitted fast round the outer side of the needle tube may be allowed to pass through the orifice into the sheath, and the case having a length such that the hub and the cap may be completely incased therein, with the needle tube incased within the sheath, the hub stopped fast to the sheath by the stop means, and the sheath extended from the cap side and fitted at one end thereof round the hub.

The attachment of the connector of this invention to the catheter, therefore, is accomplished by removing the case, connecting the outer end of a given catheter to the needle tube thrust out through the closed end of the sheath, and extracting the hub from the sheath until a full stop thereby enabling the portion of connection between the needle tube and the catheter to be completely drawn inside the sheath. Then, by removing the cap and connecting a syring, for example, to the hub, the catheter is readied for injection of a medicinal liquid, for example. After the injection, the cap may be replaced and the case fitted into position to keep the catheter from leakage until the next service.

The stop means mentioned above comprise a pair of mutually engaging parts formed one each on the outer surface of the hub and the inner surface of the sheath. One of the engaging parts may be a flat recess or protuberance of a stated length and may be so constructed that it will allow the other engaging part to slide thereon and come to a stop at either of the opposite ends thereof.

The orifice formed in the closed end of the aforementioned sheath plays the part of retaining the catheter fast in position after the portion of connection between the connecting needle and the catheter has been drawn completely inside the sheath. It, therefore, has a diameter slightly greater than the outside diameter of the catheter. When the portion of connection between the connecting needle and the catheter is in the process of being drawn into the sheath, therefore, there is a possibility that the edge of the catheter will collide into the closed end of the sheath and consequently come loose. The possibility of this accident must be precluded. It is, therefore, advantageous that the circular corner formed where the wall surface defining the orifice formed in the closed end of the sheath intersects the outer surface of the closed end should be rounded or chamferred enough for the catheter to be smoothly drawn into the sheath. Matched screws, matched tapers and other forms of coupling may be available for the union between the hub and the cap and that between the hub and the syringe. Among other forms of coupling, the coupling of matched screws is particularly advantageous because the syringe, for example, can be fastened with perfect reliability to the connector for the catheter. To permit the adoption of this particular coupling, the hub and the sheath which are fitted slidably to each other must not produce relative rotation to each other. This is because it is difficult to couple the hub and the cap, for example, or separate them and, at the same time, keep the sheath fast in position if the hub and the sheath are suffered to rotate relative to each other. It becomes necessary, therefore, that the hub should be shaped in an oval or angular cross section instead of a circular cross section and the interior of the sheath shaped in a matched cross section. Consequently, the hub may be slidably fitted into the sheath in the axial direction and it will never be allowed to rotate around itself relative to the sheath. When the hub and the cap are designed to be coupled by means of matched tapers, for example, instead of matched screws, the hub and the sheath may be rotatably fitted to each other.

BRIEF DESCRIPTION OF THE DRAWINGS

FIG. 1 is a longitudinal cross section of a typical embodiment of the connector for a catheter of this invention, in a state before use, FIG. 2 is a longitudinal cross section illustrating the connector of FIG. 1, with the case removed from the position of FIG. 1 and the connector connected to a catheter, FIG. 3 is a cross section taken along the line III—III in the diagram of FIG. 2, FIG. 4 is a longitudinal cross section illustrating the connector of FIG. 1, with the portion of connection between the needle tube and the catheter moved from the position of FIG. 2 and embraced within the sheath and the cap removed and the syringe attached in position, FIG. 5 is a longitudinal cross section illustrating the connector, with the cap replaced in position from the state of FIG. 7 and the case further fitted on the cap, and FIGS. 6 and 7 are longitudinal cross sections illustrating essential parts of other embodiments of this invention.

PREFERRED EMBODIMENT OF THE INVENTION

As illustrated in FIGS. 1-5, the connector for the indwelling catheter is an assembly of five members, i.e. a needle tube, a hub 12, a cap 14, a sheath 16 and a case 18. The needle tube 10 is made of a hollow stainless steel tube, for example, and has no sharp cutting surface but a blunt edge at the leading end. The hub 12 provided at the leading end thereof with the needle tube 10 which has been joined therein is molded of a thermoplastic resin such as polypropylene, polyethylene or polyvinyl chloride. The cap 14 is attached to the rear end of the hub 12. It is adapted to be fitted so tightly to the hub 12 as to keep the interior of the hub 12 sealed watertightly. The coupling of the cap 14 and the hub 12 is effected by means of matched screws; one flange 20 equivalent to one thread is formed on the outer surface of the edge of the hub 12 and one female thread 22 adapted to fall outside the hub 12 is formed on the cap 14. Besides, a tapered cylindrical sufface 24 diverging toward the end face is formed on the inner surface of the rear end of the hub 12 and a projected part 28 containing a male tapered cylindrical surface 26 adapted to border on the inner surface of the hub 12 is formed on the cap 14 to permit coupling of the hub 12 and the cap 14 by means of matched tapers. The sheath 16 is a blind cylinder formed of a transparent or translucent thermoplastic resin such as polypropylene, polyethylene or polyvinyl chloride, possessed of a closed end 30 at one side, and adapted to admit the hub 12 from the needle tube 10 side and fit itself round the outer side of the hub 12. It is provided in the closed end 30 thereof with an orifice 32 through which the needle tube 10 is allowed to thrust out. The case 18 is also a blind cylinder made of the same thermoplastic resin as mentioned above, possessed of a closed end 34 at one side, and adapted to admit the sheath 16 from the closed end 30 side and fit itself detachably round one end of the sheath 16.

The hub 12 and the sheath 16 have stated length $2 l_2$ and $l_3$ respectively such that the hub 12 is free to move inside the sheath 16 from the position at which the needle tube 10 is thrust from the orifice 32 to a stated length $l_1$ as illustrated in FIG. 1 to the position at which it is wholly incased within the sheath 16 as illustrated in FIG. 4. Engaging means capable of stopping the hub 12 and the sheath 16 relative to each other at the position at which the needle tube 10 is fully thrust out of the orifice 32 as illustrated in FIG. 1 and at the position at which the needle tube 10 is wholly incased within the sheath 16 as illustrated in FIG. 4 are formed on the outer surface of the hub 12 and on the inner surface of the sheath 16. In the present embodiment, the engaging means are two pairs each of protuberances 40a, 42a formed one pair each on the side 36 and the opposite side 38 of the outer surface of the hub 12 to a height enough substantially to touch the inner surface of the sheath 16 as separated by a stated distance of $l_4$ and two pairs each of notches 40b, 42b formed outside the protuberances as illustrated in FIGS. 2–3. Between the protuberances 40a, 42a, flat recesses 36, 38 are formed to give rise to voids between the outer surface of the hub 12 and the inner surface of the sheath 16. The engaging means on the sheath 16 are a pair of protuberances 48 formed one pair each on the corresponding sides 44, 46 of the inner surface to a height enough substantially to touch the outer surface of the hub 12 as mentioned above. The engaging means described above are required to be formed in at least one portion of the circumferential extent of the hub 12 and the sheath 16. In the illustrated embodiment, they are formed in two opposite portions.

The diameter D of the orifices 32 perforated in the closed end 30 of the sheath 16 is such that when the needle tube 10 thrust the orifice 32 is retracted into the sheath with an indwelling catheter 52 connected to the leading end thereof, the indwelling catheter 52 which has been fitted fast round the outer surface of the needle tube 10 and has consequently had its outside diameter increased may be passed through the orifice. The case 18 has a stated length $_5$ such that it may fit itself round the outer surface of one end of the sheath 16 from the cap 14 side and incase the hub 12 and the cap 14 when the needle tube 10 is embraced inside the sheath 16, the hub 12 is stopped relative to the sheath 16 because of the engagement between the notches 40b closer to the needle tube 10 and the protuberances 48, and the cap is attached fast to the hub 12 as illustrated in FIG. 5. The wall surface defining the orifice 32 formed in the closed end 30 of the sheath 16 is curved to enable the indwelling catheter 52 to be smoothly drawn into the sheath 16 and, at the same time, to prevent the indwelling catheter 52 already held inside the sheath 16 against possible deformation under some external force exerted via the orifice 32. As illustrated in FIG. 3, the sheath 16 is fitted round the outer surface of the hub 12 in a state now allowed to produce any relative rotation. The means for precluding this relative rotation may be flat faces 54, 56 at least in one position, or at two positions, for example, on the outer surface of the hub and flat faces 58, 60 formed correspondingly on the inner surface of the shath 16 as illustrated in FIG. 3. Alternatively, they may be matched ridges and grooves formed in the axial direction at least one pair each on the hub 12 and the sheath 16.

The case 18 is adapted so that it may be fitted round the outer surface of one end part of the sheath 16 in one state and it may then be removed from the sheath 16 and fitted round the outer surface of the opposite end part of the sheath 16 in the other state. To prevent the case from inseparably embracing the sheath 16 and the inner surface of the closed end 34 of the case from colliding into the leading end of the needle tube 10 and damaging the leading end, the sheath 16 is provided on the outer surface thereof with a flange 62 one size larger. The case 18, therefore, comes into intimate contact with the flange 62 when it is fitted round the sheath 16. On both sides of the flange 62, there are formed at least three, four in the illustrated embodiment, of ridges 64 in the axial direction. These ridges 64 are immobilized by being covered with the case 18. Annular grooves may be formed one each along the opposite edges of the flange 62 and annular ridges correspondingly formed on the inner surface close to the open end of the case 18, so that the engagement between the grooves and the ridges will secure the case 18 to the sheath 16.

The connector for the catheter which is constructed as described above is offered for use in the state illustrated in FIG. 1. For shipment, the connector with all the components thereof assembled as completely incased in the case 18 is placed in a gas-permeable wrapping bag. The bag is then sealed and sterilized with ethylene oxide gas.

Now, the method for the use of this connector will be described. The connector for the catheter is attached to a given catheter 52 after this catheter 52 has been secured to the blood vessel, for example, by the hollow needle method. From the connector which is held in the state illustrated in FIG. 1, the case 18 is removed. To the needle tube 10 which has been consequently exposed, the catheter 52 is immediately connected as illustrated in FIG. 2. After the connection of the needle tube 10 to the catheter 52 is completed, the cap 14 still held on the hub is nipped by fingers and drawn away from the sheath 16 until it is brought to a stop so that the portion of connection between the needle tube 10 and the indwelling catheter 52 may be drawn inside the sheath 16. In this case, since the inlet side edge of the orifice 32 is rounded or chamferred, the edge of the catheter 52 is not repelled by the closed end 30 of the sheath 16. The catheter 52, therefore, is smoothly passed through the orifice. The possibility of the catheter 52 sustaining damage on the outer surface thereof during the passage through this orifice is remote. When the cap 14 nipped by the fingers is drawn away the sheath 16 until a complete stop as described above, the hub 12 slides inside the sheath 16 and the protuberances 48 formed on the inner surface of the sheath 16 side on the outer surface of the hub 12 between the protuberances 40, 42 formed on the outer surface of the hub 12 and eventually ride past the protuberances 40a and fall into the notches 40b, with the result that the hub 12 is stopped relative to the sheath 16. Then, the cap 14 is turned and removed and a tip portion of syringe 55 is attached as illustrated in FIG. 4 to effect desired transfer of a medicinal liquid. When the connector is used on a catheter which is inserted into the blood vessel, the catheter 52 is kept closed such as with pincers or finger tips to prevent outflow of blood until the syringe 66 is attached. Before the syringe 66 is attached, the hub 12 is kept filled with physiological saline solution containing heparin to keep the interior of the hub 12 from invasion of air. After the transfer of medicinal liquid has been effected as described above, the root of the catheter 52 is closed with pincers, the syringe 55 is removed, then the cap 14 is replaced in position, and the case 18 which has been removed at first as described above is slipped on the outer surface of the sheath 16 so as to embrace therein the cap 14 and the hub 12 which has been drawn out of the sheath 16. This will complete one cycle of treatment with the catheter. The attachment of the cap 14 and the syringe 55 to the hub 12 or the detachment thereof from the hub 12 may be effected by holding the sheath 16 fast in the hand because the hub 12 is not allowed to rotate relative to the sheath 16.

The means for relative stop of the hub and the sheath may be formed with one of the stop means formed on the outer surface of the hub and the other stop means formed on the inner surface so that the hub and the sheath are allowed to slide against each other over a stated distance and they are brought into mutual engagement at each of the opposite ends of the distance so fixed. In the embodiment illustrated in FIG. 6, the stop means are protuberances 142 fromed on the outer surface of the hub 112 and grooves 136 of a stated length formed on the inner surface of the sheath 116 and recesses 140 formed one each at the opposite ends of the grooves 136 to a depth below the grooves. When the coupling of the hub 112 and the cap is effected by means of mutual insertion as with matched tapers instead of matched threads, the hub 112 is allowed to rotate relative to the sheath 116. Thus, the hub 112 and the sheath 116 may be coupled in a mutually rotatable state. The flange 162 contains annular grooves along the opposite edges thereof and the case 1118 contains corresponding annular ridges 168 on the inner surface of the open end edge thereof. Thus, the case 118 can be stopped to the sheath 116 by causing the annular ridges 168 to fall into the annular grooves 166.

In the arrangement described above, the stop means may be obtained by giving a state reduced diameter to a stated length of the hub 212 less the opposite end portions, forming annular engaging grooves 240 of a still smaller diameter one each at the opposite ends of the small-diameter portion 236, and forming corresponding annular ridges 242 on the inner surface of the sheath 216. Alternatively, they may be obtained by fixing two annular magnets as separated by a stated distance on the outer surface of the hub and fixing one annular magnet on the inner surface of the sheath.

As described above, the connector contemplated by this invention comprises a hub of a stated length provided at the leading end thereof with a needle tube and having a cap attached to the rear end thereof, a sheath adapted to admit therein the hub from the needle tube side, provided at the leading end thereof with a closed end containing therein an orifice for allowing the needle tube to be thrust out therethrough and retracted therethrough, and a case adapted to be slipped on either end of the sheath. When the connector is supplied to a physician, for example, the needle tube is protected by the case. Prior to use, the physician is only required to remove the case. Then, the needle tube is exposed as thrust out of the orifice and, therefore, can be quickly and very simply connected to a catheter. Once this connection is made, the cap is nipped by the fingers and drawn off the sheath to admit the portion of connection between the needle tube and the catheter inside the sheath. Since the closed end of the sheath supports the catheter fast in position, the posibility of the needle tube being fractured by external force and the possibility of the catheter being fractured at the portion of connection with the needle tube or coming loose are precluded. After the transfer of a medicinal liquid through the catheter, the case can be slipped over the sheath so as to embrace therein the cap and the hub. Because of this construction, the number of components which go to make up the connector can be minized. Further, since the case provide double protection, the otherwise possible contamination by leakage through the cap side during the prolonged of the catheter in the patient's body can be precluded. This invention has such outstanding operation and effect.

When this invention, in one aspect, has protuberances and notches formed respectively on the outer surface of the hub and on the inner surface of the sheath, possible accidental separation of the hub and the sheath is prevented and the connection of the catheter to the connecting needle becomes easy. When, in another aspect of this invention, the corner formed where the wall surface defining the orifice formed in the closed end of the sheath interescets with the outer surface of the closed end is round or chamferred, the catheter can be smoothly admitted into the sheath and the closed end of the sheath holds the catheter fast in position. Owing to the fast retention thus obtained, an external force tending to undo the connection of the catheter to the needle tube is effectively repelled and the catheter itself is prevented from being bent. When, in still another aspect of this invention, the hub and the sheath are coupled with each other in such a state prohibiting relative rotation, this arrangement permits the coupling of the hub and the cap and that of the hub and the syringe to be effected by means of matched threads. Thus, there is no possibility of the cap being accidentally removed from the hub.

What is claimed is:

1. A connector for a catheter, which comprises:
   a hub provided at the leading end thereof with a hollow needle tube;
   a cap capable of detachably attaching itself to the rear end of the hub and watertightly sealing the interior of the hub;
   a sheath in the shape of a blind cylinder for admitting therein the hub from the needle tube side while allowing itself to be slidably fitted around the outer side of the hub, the blind cylinder being provided in the closed end thereof with an orifice for permitting the needle tube to be thrust out therethrough; and
   a case of the shape of a blind cylinder for admitting therein the sheath from the closed end side thereof while allowing itself to be detachably fitted round one end part of the sheath;
   the hub and the sheath having relative lengths such that the hub is free to move inside the sheath from a position at which the needle tube is fully thrust out through the orifice to a position at which it is wholly embraced within the sheath;
   the hub and the sheath being provided on the outer and inner surfaces thereof respectively with stop means for stopping the hub and the sheath relative to each other at the position at which the needle tube is fully thrust out through the orifice to the position at which it is wholly embraced within the sheath;

the orifice having a diameter such that when the needle tube thrust out through the orifice is retracted to be embraced again within the sheath, the indwelling catheter meanwhile fitted fast around the outer side of the needle tube is allowed to pass through the orifice into the sheath; and the case having a length such that the hub and the cap may be completely incased therein, with the needle tube incased within the sheath, the hub stopped fast to the sheath by the stop means, and the case extended from the cap side of the hub and fitted at one end thereof around the sheath.

2. A connector according to claim 1, wherein at least one pair of stop means is provided, one on the outer surface of the hub and the other on the inner surface of the sheath, and one of the pair of stop means comprises a pair of protuberances and a flat recess formed between said a pair of protuberances, and said one stop means be engageable with the other stop means.

3. A connector according to claim 2, wherein the other stop means formed on the inner surface of the sheath comprises a pair of protuberances formed correspondingly to the pair of protuberances on the outer surface of the hub.

4. A connector according to claim 1, wherein the wall surface defining the orifice formed in the closed end of the sheath is curved.

5. A connector according to claim 1, wherein the sheath is fitted on the outer surface of the hub so that it is non-rotatable relative to the hub.

6. A connector according to claim 1, wherein the stop means comprises protuberances formed on the outer surface of the hub and grooves of given length and notches formed at the opposite ends of said grooves to a greater depth.

7. A connector according to claim 1, wherein the stop means comprises a portion of a reduced diameter formed in a given length of the hub less than the opposite end portions, annular engaging grooves formed one each at the opposite ends of said reduced-diameter portion in a still smaller diameter, and annular protuberances formed correspondingly on the inner surface of the sheath.

8. A connector according to claim 1, wherein the hub is provided on the outside of the open end thereof with a flange adapted to be helically joined with the cap.

9. A connector according to claim 5, wherein means is provided for rendering the sheath non-rotatable relative to the outer surface of the hub, said means comprising a flat face formed in at least one portion of the outer surface of the hub and a corresponding flat face formed on the inner surface of the sheath.

10. A connector according to claim 1, wherein at least one flange is formed on the outer surface of the sheath.

* * * * *

UNITED STATES PATENT AND TRADEMARK OFFICE
CERTIFICATE OF CORRECTION

PATENT NO. : 4,417,887
DATED : November 29, 1983
INVENTOR(S) : Isei KOSHI

It is certified that error appears in the above-identified patent and that said Letters Patent is hereby corrected as shown below:

COLUMN 9 (claim 2), line 25, after "one stop means" change

"be" to --being--.

Signed and Sealed this

Nineteenth Day of June 1984

[SEAL]

Attest:

GERALD J. MOSSINGHOFF

Attesting Officer

Commissioner of Patents and Trademarks